(12) United States Patent
Taniguchi et al.

(10) Patent No.: US 11,435,295 B2
(45) Date of Patent: Sep. 6, 2022

(54) SENSOR ELEMENT AND PACKAGED BODY

(71) Applicant: Yokogawa Electric Corporation, Tokyo (JP)

(72) Inventors: Koichi Taniguchi, Tokyo (JP); Mitsuhiro Iga, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 287 days.

(21) Appl. No.: 16/555,349

(22) Filed: Aug. 29, 2019

(65) Prior Publication Data

US 2020/0072757 A1 Mar. 5, 2020

(30) Foreign Application Priority Data

Sep. 5, 2018 (JP) .............................. JP2018-165871

(51) Int. Cl.
*G01N 21/80* (2006.01)
*G01N 21/47* (2006.01)
(Continued)

(52) U.S. Cl.
CPC ............ *G01N 21/80* (2013.01); *A01G 25/167* (2013.01); *G01D 11/245* (2013.01); *G01K 11/12* (2013.01);
(Continued)

(58) Field of Classification Search
CPC ........ G01N 21/80; G01N 21/47; G01N 21/55; G01N 33/246; G01N 21/64; G01N 21/59; G01N 21/6428; G01N 2021/1793; G01N 2021/1797; G01N 2021/7786; G01N 2201/0214; G01N 2021/7773; G01N 21/81; G01N 21/78; G01K 11/12; A01G 25/167; A01B 79/005; G01D 5/26; G01D 5/48; G01D 11/245

See application file for complete search history.

(56) References Cited

U.S. PATENT DOCUMENTS 4,063,452 A 12/1977 Bradshaw
4,762,426 A 8/1988 Foss
(Continued)

FOREIGN PATENT DOCUMENTS

JP 52-7792 A 1/1977
JP 11-225509 A 8/1999
(Continued)

OTHER PUBLICATIONS

Translation of KR20170101372A, Lee, Min Hee, Sep. 6, 2017 (Year: 2017).*
(Continued)

*Primary Examiner* — Samuel P Siefke
*Assistant Examiner* — Henry H Nguyen
(74) *Attorney, Agent, or Firm* — Rankin, Hill & Clark LLP (57) ABSTRACT

A sensor element is used to collect environment information on a surface of the earth or a surface layer of the earth by being scattered in a target region where the environment information is collected. At least one of reflection properties, transmission properties, absorption properties, or luminescence properties with respective to an electromagnetic wave with a specific wavelength, or light emitting properties changes in accordance with an environment.

13 Claims, 6 Drawing Sheets

(51) Int. Cl.
*G01N 21/55* (2014.01)
*G01N 33/24* (2006.01)
*G01N 21/64* (2006.01)
*G01K 11/12* (2021.01)
*G01N 21/59* (2006.01)
*G01N 21/81* (2006.01)
*G01N 21/78* (2006.01)
*G01N 21/17* (2006.01)
*G01N 21/77* (2006.01)
*A01G 25/16* (2006.01)
*G01D 11/24* (2006.01)
*A01B 79/00* (2006.01)

(52) U.S. Cl.
CPC ............ *G01N 21/47* (2013.01); *G01N 21/55* (2013.01); *G01N 21/59* (2013.01); *G01N 21/64* (2013.01); *G01N 21/78* (2013.01); *G01N 21/81* (2013.01); *G01N 33/246* (2013.01); *A01B 79/005* (2013.01); *G01N 2021/1793* (2013.01); *G01N 2021/1797* (2013.01); *G01N 2021/7773* (2013.01); *G01N 2201/0214* (2013.01)

(56) References Cited

U.S. PATENT DOCUMENTS

| | | | |
|---|---|---|---|
| 2002/0131900 A1* | 9/2002 | Jensen | G01N 33/84 422/82.05 |
| 2003/0099589 A1 | 5/2003 | Hero et al. | |
| 2007/0211985 A1* | 9/2007 | Duer | G01N 21/553 385/12 |
| 2012/0140224 A1* | 6/2012 | Switkes | G01N 21/78 356/369 |
| 2013/0213110 A1* | 8/2013 | Papadimitrakopoulos | G01N 33/52 73/1.02 |
| 2016/0063420 A1* | 3/2016 | Tomii | G06Q 10/06314 705/7.24 |
| 2017/0045487 A1* | 2/2017 | Bauer-Reich | H04B 7/1851 |
| 2018/0100807 A1 | 4/2018 | Abdo et al. | |

FOREIGN PATENT DOCUMENTS

| | | | |
|---|---|---|---|
| JP | 2005-255580 A | | 9/2005 |
| JP | 2013-113614 A | | 6/2013 |
| JP | 2014-110784 A | | 6/2014 |
| JP | 2015-141537 | | 8/2015 |
| JP | 2015-212235 A | | 11/2015 |
| JP | 2016015940 A | * | 2/2016 |
| JP | 2017-195732 A | | 10/2017 |
| KR | 20170101372 A | * | 9/2017 |
| WO | 2017/098222 A1 | | 6/2017 |

OTHER PUBLICATIONS

Translation of JP2016015940A, Ito, Nobuyuki, Feb. 1, 2016 (Year: 2016).*

* cited by examiner

SENSOR ELEMENT AND PACKAGED BODY

BACKGROUND

Technical Fields

The present invention relates to a sensor element and a packaged body. Priority is claimed on Japanese Patent Application No. 2018-165871, filed on Sep. 5, 2018, the contents of which are incorporated herein by reference.

Related Art

A temperature, a humidity, an air pressure, and other kinds of environment information on the surface of the earth or a surface layer of the earth may be required in various fields such as the fields of agriculture, fishery, mining, and the like. In an example of the field of agriculture, environment information such as water content, a temperature, pH, and the amount of sunshine for soil in which agricultural crops are produced may be required. It is possible to recognize locations where water or agricultural chemicals are insufficient and the amounts of insufficiency, for example, if such environment information is obtained and thereby to realize optimization of the amounts of water or agricultural chemicals used (only required amounts of water and agricultural chemicals are scattered at locations where they are required).

In recent years, industrialization and an increase in scale of the field of agriculture have been attempted in order for a smaller number of workers to produce a larger amount of agricultural crops at low costs in the field of agriculture. On an industrialized large scale farm, watering on a broad farm is performed using sprinklers, for example, seed scattering and agricultural chemical application are performed using aircrafts or helicopters, and agricultural crops (for example, grains such as rice, wheat, soybeans, and corn) are harvested using large combine harvesters.

On such a large scale farm, water and agricultural chemicals exceeding required amounts are used in many cases, and there are thus concerns of environmental problems. For example, there is a concern about a probability of drought due to depletion of water resources since a large amount of water is used. Also, there is a concern about a probability of pest damage due to mass generation of insects that have resistance against agricultural chemicals since large amounts of agricultural chemicals are used. Therefore, in order to realize sustainable agriculture while protecting the environment, it is also desirable to obtain environment information such as water content, a temperature, pH, and the amount of sunshine and to realize optimization of the amounts of water and agricultural chemicals used even in a large-sale farm.

Japanese Unexamined Patent Application Publication 2015-141537 discloses a field observation system adapted to observe a state of a field for supporting farm work. The field observation system has a sensing unit provided with various sensors for measuring temperature and the like and a communication unit, includes a field observation device (slave device) located in the field and a management device (master device), and is configured such that a transmission request is provided to the field observation device by the management device in a case in which a worker who brings the management device with him/her approaches the field observation device and a measurement result stored in the field observation device is transmitted to the management device through near-field wireless communication or the like.

Incidentally, in the field observation system disclosed in Japanese Unexamined Patent Application Publication 2015-141537 described above, a distribution of environment information (a two-dimensional distribution of water content contained in soil, for example) can be obtained by installing a plurality of field observation devices that serve as slave devices. Therefore, for example, it is also considered to be possible to obtain a distribution of environment information even on the aforementioned large scale farm if an enormous number of field observation devices are located at specific intervals.

However, since the field observation devices used in the field observation system disclosed in Japanese Unexamined Patent Application Publication 2015-141537 described above operate using batteries, it is necessary to periodically replace the batteries. Since an enormous number of field observation devices are located on extensive farmland of a large scale farm and significant efforts and a long period of time are required to replace batteries of all the field observation devices, there is a problem that it is difficult to address this work by a small number of workers.

Also, in the field observation system disclosed in Japanese Unexamined Patent Application Publication 2015-141537 described above, it is necessary for the worker who brings the management device with him/her to approach the field observation devices in order to obtain measurement results stored in the field observation devices. Since an enormous number of field observation devices are located on the extensive farmland of the large scale farm, it is necessary for the operator who brings the management device with him/her to walk around the extensive farmland and to approach all the field observation devices in order to obtain the measurement results of all the field observation devices, significant efforts and a long period of time are required, and there is a problem that it is difficult to address the replacement by a small number of workers.

SUMMARY

A sensor element is used to collect environment information on a surface of the earth or a surface layer of the earth by being scattered in a target region where the environment information is collected. At least one of reflection properties, transmission properties, absorption properties, or luminescence properties with respective to an electromagnetic wave with a specific wavelength, or light emitting properties changes in accordance with an environment.

Further features and aspects of the present disclosure will become apparent from the following detailed description of exemplary embodiments with reference to the attached drawings.

DETAILED DESCRIPTION OF THE EMBODIMENTS

The embodiments of the present invention will be now described herein with reference to illustrative preferred embodiments. Those skilled in the art will recognize that many alternative preferred embodiments can be accomplished using the teaching of the present invention and that the present invention is not limited to the preferred embodiments illustrated herein for explanatory purposes.

An aspect of the present invention is to provide a sensor element that can be used in an environment information collecting system capable of obtaining environment information on the surface of the earth or the surface layer of the earth in a short period of time in an easy manner without any need of great effort, and to provide a packaged body in which the sensor element is packaged by a packaging material.

Hereinafter, an environment information collecting system and an aircraft according to an embodiment of the invention will be described in detail with reference to the drawings.

(Environment Information Collecting System)

Figure 1:
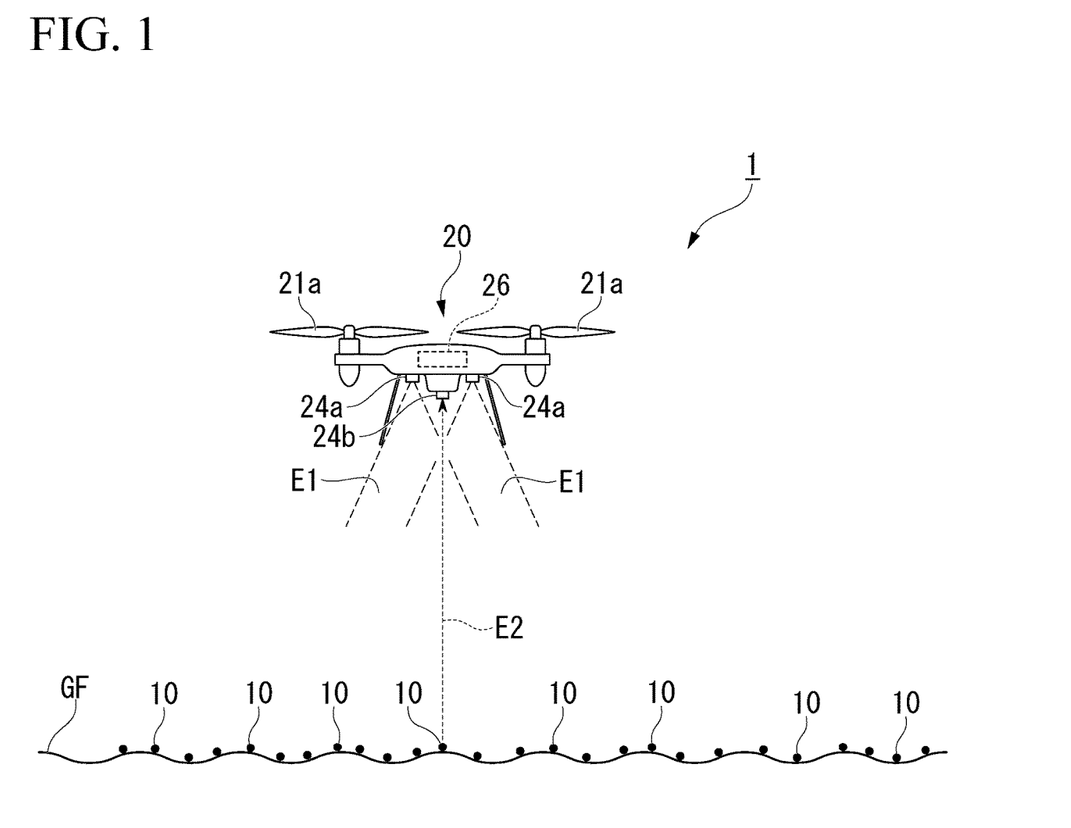
FIG. 1 is a diagram illustrating an outline of an environment information collecting system according to an embodiment of the invention.

FIG. 1 is a diagram illustrating an outline of an environment information collecting system according to an embodiment of the invention. As illustrated in FIG. 1, an environment information collecting system 1 according to the embodiment includes sensor elements 10 scattered on the ground surface GF and a drone 20 (aircraft) which transmits an electromagnetic wave E1 with a specific wavelength to the ground surface GF on which the sensor elements 10 are scattered, and receives an electromagnetic wave E2 obtained from the sensor elements 10, thereby collecting environment information (for example, water content, a temperature, pH, the amount of sunshine, and the like) on the ground surface GF.

The sensor elements 10 are elements, which are scattered in a region (target region TA: see FIG. 7) where environment information on the ground surface GF is collected, in which at least one of reflection properties, transmission properties, absorption properties, or luminescence properties with respect to the electromagnetic wave E1 with a specific wavelength, or light emitting properties changes in accordance with the surrounding environment. For example, the sensor elements 10 are elements in which reflection properties and transmission properties with respect to the electromagnetic wave E1 change in accordance with a temperature on the ground surface GF, are elements in which intensity and the like of fluorescent light or phosphorescent light emitted by the sensor elements 10 changes in accordance with the water content or pH on the ground surface GF, or are elements in which light emission intensity of chemical (self-) light emission changes in accordance with the temperature on the ground surface GF (an element in which light emitting properties change). Note that elements that contain a light-emitting enzyme such as luciferase can be used as the elements in which light emitting properties change.

A change in the aforementioned properties may be a quantitative change or a qualitative change. As an example of a quantitative change, it is possible to exemplify a case in which at least one of reflectance, a transmission rate, or an absorption rate with respect to the electromagnetic wave E1 with the specific wavelength, a conversion rate of the electromagnetic wave E1 into fluorescent light or phosphorescent light, or light emitting intensity changes in accordance with a change in environment. As an example of a qualitative change, it is possible to exemplify a case in which at least one of a reflection wavelength, a transmission wavelength, an absorption wavelength, or a luminescence discharge wavelength with respect to the electromagnetic wave E1 with the specific wavelength, or a light emitting wavelength changes in accordance with a change in environment.

The sensor elements 10 are solid bodies and preferably have a predetermined shape. The shape of the sensor elements 10 is not particularly limited and can be a spherical shape, a plate shape, a cubic shape, a columnar shape, a polygonal pillar shape, a cone shape, a polygonal pyramid, or another arbitrary shape. In regard to the plate shape, a shape with a circular, oval, polygonal, or rectangular plan-view shape can be exemplified. Note that all the aforementioned predetermined shapes are exemplified as the shape of the sensor elements, but the shape of the sensor elements may be irregular.

The number of sensor elements 10 scattered on the ground surface GF is arbitrarily decided. For example, about several hundred to several hundred thousand sensor elements 10 per 1 [m$^2$] may be used in the field of agriculture. Note that the number of sensor elements 10 exemplified herein is just an example and it should be noted that the number may be smaller or larger than the exemplified number.

The sensor elements 10 may or may not be biodegradable. For example, it is desirable that the sensor elements 10 used in the field of agriculture be biodegradable since the sensor elements 10 are used by being scattered on extensive farmland and it is difficult to collect the sensor elements 10. It is desirable that such sensor elements 10 are degraded through biodegradation after a period corresponding to a period from seed scattering of agricultural crops to harvesting of the agricultural crops, for example, elapses. On the other hand, it is preferable that the sensor elements 10 used for the purpose of measuring temperatures in a region limited to some extent (for example, a road or the like) for a long period of time, for example, not be biodegradable since the sensor elements 10 are not collected for a long period of time and it is considered to be not very difficult to collect the sensor elements. Note that details of the sensor elements 10 will be described later.

The drone 20 has a plurality of (four, for example) blades 21a (rotary wings) and can autonomously fly along a preset flight route. Note that the drone 20 may be adapted to receive a control signal transmitted from the outside and fly in accordance with the received control signal. The drone 20 includes a transmitter 24a that transmits the electromagnetic waves E1 with a specific wavelength to the ground surface GF and a receiver 24b that receives the electromagnetic wave E2 obtained from the sensor elements 10. Note that the number of the transmitters 24a and the receivers 24b may be one or more.

As the electromagnetic wave E1 transmitted from the transmitter 24a, an electromagnetic wave with an appropriate wavelength (frequency) in consideration of a state of the ground surface GF on which the sensor elements 10 are scattered, properties of the sensor element 10, and the like is used. As the electromagnetic wave E1, a millimeter wave, a terahertz wave, an infrared ray, a visible ray, an ultraviolet ray, an X-ray, or the like can be used. For example, since the sensor elements 10 used in the field of agriculture are mixed in and scattered with a fertilizer or a pesticide, there is a case in which the sensor elements 10 are present in the ground (for example, in a range of about several tens of [cm] from the ground surface GF). In such a case, the electromagnetic wave E1 with a wavelength that has permeability to some extent with respect to soil, for example, is used.

Note that the wavelength of the electromagnetic wave E2 obtained from the sensor elements 10 is the same as or is different from the wavelength of the electromagnetic wave E1 transmitted from the drone 20 in accordance with properties of the sensor elements 10. For example, in a case in which the sensor elements 10 have properties in which reflection properties and transmission properties with respect to the electromagnetic wave E1 change in accordance with the surrounding environment, the wavelength of the electromagnetic wave E2 is the same as that of the electromagnetic wave E1. On the other hand, in a case in which the sensor elements 10 have properties in which intensity or the like of emitted fluorescent light or phosphorescent light changes in accordance with the surrounding environment, the wavelength of the electromagnetic wave E2 is different from that of the electromagnetic wave E1. Also, the drone 20 includes a scattering device 26 employed to scatter the sensor elements 10 in a target region TA or the like. Note that details of the details of the drone 20 will be described later.

(Sensor Element)

Hereinafter, an embodiment of the sensor element according to the invention will be described.

The sensor element according to the embodiment is used to collect environment information on the surface of the earth or a surface layer of the earth, and is used by being scattered in a target region where the aforementioned environment information is collected, and at least one of reflection properties, transmission properties, absorption properties, or luminescence properties with respect to an electromagnetic wave with a specific wavelength, and light emitting properties changes in accordance with the environment.

The aforementioned environment information is not particularly limited as long as it is a measurable item and is preferably at least one of water content, a temperature, a concentration of nutrients such as a fertilizer, a constituent ratio of bacterial species in the ground, or pH.

The sensor element according to the embodiment may be employed such that the aforementioned environment information is at least either the water content or the temperature and the shape thereof changes in accordance with a change in at least one of these changes.

Figures 2A, 2B:
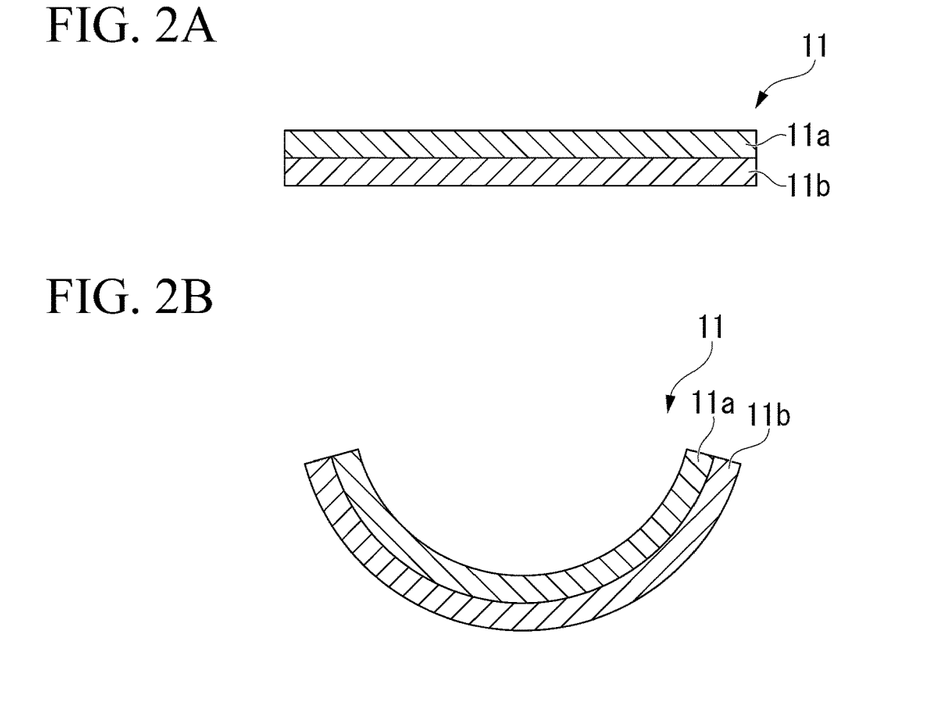
FIG. 2A is a sectional view illustrating a first example of a sensor element used in the environment information collecting system according to an embodiment of the invention.
FIG. 2B is a sectional view illustrating a first example of a sensor element used in the environment information collecting system according to an embodiment of the invention.

FIG. 2A and FIG. 2B are sectional views illustrating a first example of a sensor element used in an environment information collecting system according to an embodiment of the invention. The sensor element 11 illustrated in FIG. 2 and FIG. 2B has a shape that changes in accordance with a change in temperature. As illustrated in FIG. 2A, the sensor element 11 includes a first base material 11a and a second base material 11b, and a coefficient of thermal expansion of the first base material 11a depending on a temperature is different from a coefficient of thermal expansion of the second base material 11b depending on a temperature. The shape of the sensor element is a disk shape with a major axis of about several [mm] and a thickness of about several hundreds of [μm], for example.

In a case in which the coefficient of thermal expansion of the second base material 11b is greater than the coefficient of thermal expansion of the first base material 11a, for example, the sensor element 11 is bent, and the shape thereof changes as illustrated in FIG. 2B if the ambient temperature increases. The occurrence of such a change in shape leads to changes in reflection properties and transmission properties with respect to the electromagnetic wave E1.

If the sensor element 11 illustrated in FIG. 2A is deformed as illustrated in FIG. 2B, the size of the sensor element 11 in a plan view decreases (the area decreases). The size of the sensor element 11 in a plan view is considered to decrease in proportion to an ambient temperature rise, for example. Therefore, a substance with high reflectance with respect to the electromagnetic wave E1 may be caused to adhere (or is applied as a coating) to the surface of the sensor element 11, for example, so that the reflectance of the sensor element 11 changes in accordance with a change in size of the sensor element 11.

Materials of the first base material 11a and the second base material 11b may be selected in consideration of reflection properties and transmission properties with respect to the electromagnetic wave E1, a state of the ground surface GF on which the sensor element 11 is scattered, the coefficients of thermal expansion, and the like. As an example of a combination of the first base material 11a and the second base material 11b, a combination of a material with a coefficient of thermal expansion of less than 10 and a material with a coefficient of thermal expansion of equal to or greater than 10 is exemplified. As the material with the coefficient of thermal expansion of less than 10, polystyrene, an AS resin, polycarbonate, polymethyl methacrylate, a phenol resin, an epoxy resin, and the like are exemplified. As the material with the coefficient of thermal expansion of equal to or greater than 10, polyethylene, polyvinylidene chloride, polyvinylidene fluoride, polyethylene terephthalate, cellulose acetate, and the like are exemplified.

Figure 3A:
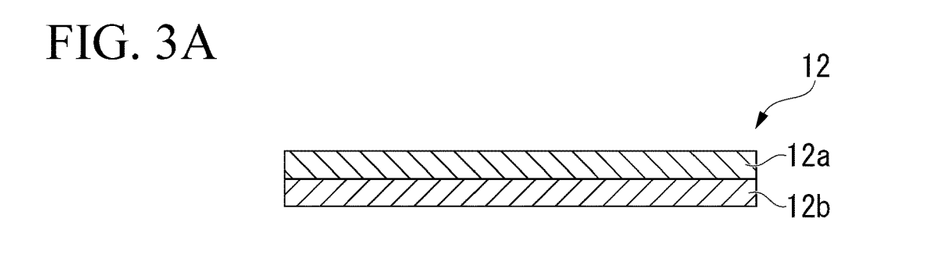
FIG. 3A is a sectional view illustrating a second example of a sensor element used in the environment information collecting system according to an embodiment of the invention.

FIG. 3 is a sectional view illustrating a second example of a sensor element used in the environment information collecting system according to an embodiment of the invention. A sensor element 12 illustrated in FIG. 3 has a shape that changes in accordance with a change in water content. As illustrated in FIG. 3(a), the sensor element 12 includes a third base material 12a and a fourth base material 12b, and a rate of change in volume of the third base material 12a depending on water retention differs from a rate of change in volume of the fourth base material 12b depending on water retention. The shape of the sensor element is a disk shape with a major axis of about several [mm] and a thickness of several hundreds of [μm], for example.

The "rate of change in volume" is defined by the following formula.

Rate of change in volume (%)=(V1−V2)/V2×100

(In the above formula, V1 represents the volume of the base material after the base material is dipped in water at a temperature of 25° C. for 15 minutes, and V2 represents the volume of the base material before V1 undergoes the aforementioned treatment after fabrication).

Figure 3B:
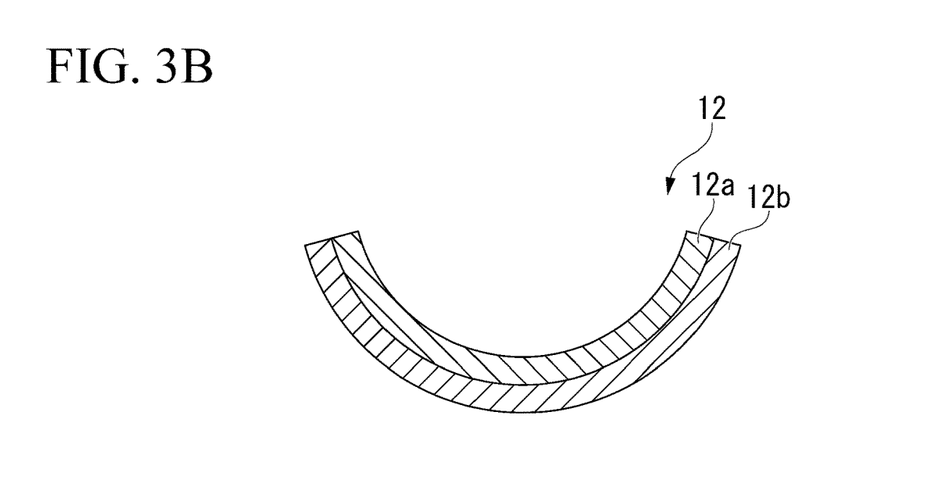
FIG. 3B is a sectional view illustrating a second example of a sensor element used in the environment information collecting system according to an embodiment of the invention.

In a case in which the rate of change in volume of the fourth base material 12b depending on water retention is greater than the rate of change in volume of the third base material 12a depending on water retention, for example, the sensor element 12 is bent, and the shape thereof changes as illustrated in FIG. 3(b) if the ambient water content rises. The occurrence of such a change in shape leads to changes in reflection properties and transmission properties with respect to the electromagnetic wave E1.

If the sensor element 12 illustrated in FIG. 3(a) is deformed as illustrated in FIG. 3(b), the size of the sensor element 12 in a plan view decreases (the area decreases). The size of the sensor element 12 in a plan view is considered to decrease in proportion to a rise in the ambient water content, for example. Therefore, a substance with high reflectance with respect to the electromagnetic wave E1 may be caused to adhere (or is applied as a coating) to the surface of the sensor element 12, for example, so that the reflectance of the sensor element 12 changes in accordance with a change in size of the sensor element 12.

Materials of the third base material 12a and the fourth base material 12b are selected in consideration of reflection properties and transmission properties with respect to the electromagnetic wave E1, a state of the ground surface GF on which the sensor element 12 is scattered, water absorption properties, and the like. For the third base material 12a, a highly crystalline polymer molded article such as a cellulose film, for example, can be exemplified. For the fourth base material 12b, a molded article of a composite polysaccharide such as a pectin film, for example, can be exemplified.

Figure 4:
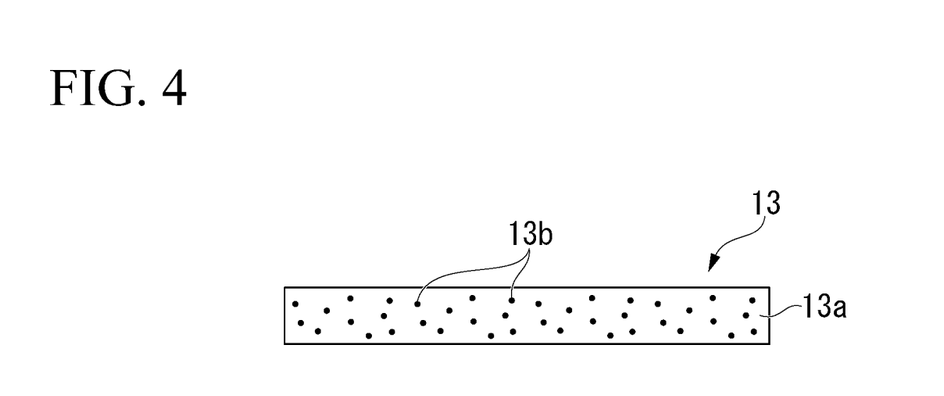
FIG. 4 is a sectional view illustrating a third example of a sensor element used in the environment information collecting system according to an embodiment of the invention.

FIG. 4 is a sectional view illustrating a third example of a sensor element used in the environment information collecting system according to an embodiment of the invention. A sensor element 13 illustrated in FIG. 4 includes a substance in which at least one of reflection properties, transmission properties, absorption properties, or luminescence properties with respect to an electromagnetic wave with a specific wavelength, or light emitting properties changes in accordance with a change in pH. As illustrated in FIG. 4, the sensor element 13 includes a pigment 13b inside a transparent base material 13a, for example, and has a disk shape with a diameter of about several [mm] and a thickness of about several hundreds of [μm], for example. Note that although FIG. 4 illustrates the pigment 13b in the form of particles for easy understanding, the pigment 13b is not necessarily granular.

The pigment 13b is a pH-responsive pigment. The pH-responsive pigment is one in which at least one of reflection properties, transmission properties, absorption properties, or luminescence properties with respect to an electromagnetic wave with a specific wavelength, or light emitting properties changes in accordance with a change in pH.

As the pH-responsive pigment, a pigment with a color changing in accordance with a concentration of hydrogen ions is exemplified, a pigment that is used as a pH indicator may also be used, and examples thereof include litmus, bromothymol blue, bromophenol blue, bromocresol purple, phenol red, phenolphthalein, methyl orange, methyl red, methyl yellow, methyl violet, thymol blue, thymol phthalein, and the like.

The pH-responsive pigment may be a pH-sensitive fluorescent pigment. As the pH-sensitive fluorescent pigment, a fluorescent pigment in which a fluorescent light color or intensity of fluorescent light changes in accordance with a concentration of hydrogen ions is exemplified, and for example, pHrodo (registered trademark), Ageladine A, CypHer 5, and the like can be exemplified.

The sensor element 13 may include one kind of pigment alone or may include two or more kinds in combination.

In a case in which the pigment 13b is a pH-sensitive fluorescent pigment, for example, if the sensor element 13 is irradiated with the electromagnetic wave E1, the pigment 13b provided in the sensor element 13 is excited, and this leads to emission of fluorescent light or phosphorescent light from the sensor element 13. The intensity or the like of the fluorescent light or the phosphorescent light changes in accordance with pH around the sensor element 13. In this manner, in a case in which the pigment 13b is a pH-sensitive fluorescent pigment, the sensor element 13 illustrated in FIG. 3 is excited by the electromagnetic wave E1, and luminescence properties thereof change in accordance with ambient pH.

The material of the base material 13a and the pigment 13b are selected in consideration of luminescence properties, a state of the ground surface GF on which the sensor element 13 is scattered, and the like.

Figure 5:
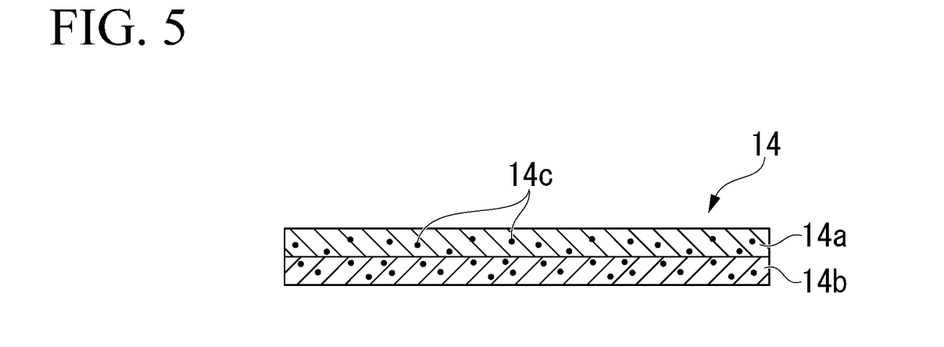
FIG. 5 is a sectional view illustrating a fourth example of a sensor element used in the environment information collecting system according to an embodiment of the invention.

FIG. 5 is a sectional view illustrating a fourth example of a sensor element used in the environment information collecting system according to an embodiment of the invention. A sensor element 14 illustrated in FIG. 5 includes a fluorescent pigment 14c. The fluorescent pigment 14c may not correspond to the aforementioned pigment in which at least one of the aforementioned properties changes in accordance with the environment. As illustrated in FIG. 5, the sensor element 14 is provided with the fluorescent pigment 14c inside the first base material 14a and the second base material 14b in the first example of the sensor element illustrated in FIG. 2A and FIG. 2B. By the sensor element 14 including the fluorescent pigment 14c, it becomes easy to distinguish the wavelength obtained from the sensor element from the other wavelengths, and precision in collecting information is thus improved.

As such a fluorescent pigment, acridine orange, auramine O, calcofluor white, ethidium bromide, fluorescein isothiocyanate, Hoechst 33258, Rhodamine B, and the like are exemplified.

The sensor element according to the embodiment may or may not be biodegradable and is preferably biodegradable.

Therefore, the sensor element according to the embodiment is preferably made of a biodegradable material. By the sensor element according to the embodiment being made of a biodegradable material, the sensor element is degraded in the target region where environment information is collected, and it is thus not necessary to collect the sensor element. Therefore, it is possible to reduce costs for the collection and to reduce an environmental impact.

As a biodegradable material, a material that can be degraded with microorganisms or enzymes such as biodegradable plastic is exemplified. As the biodegradable material, polylactic acid, polycaprolactone, polyhydroxyalkanoate, a polyhydroxy butyric acid, a polyglycolic acid, polyvinyl alcohol, casein, starch, esterified starch, cellulose, pectin, agar, gelatin, for example, are exemplified.

In addition, the sensor element according to the embodiment is preferably made of a material derived from biomass from the viewpoint of reducing an environmental impact. Also, it is preferable that the sensor element according to the embodiment contains substantially no materials derived from petroleum.

It is preferable that the sensor element according to the embodiment contain substantially no metal. In an environment information collecting system in the related art, it is essential for a sensor element to contain metal since an observation device naturally has an electronic circuit or the like. Meanwhile, since the sensor element according to the embodiment that contains substantially no metal can realize its function without including metal, metals do not contaminate a field or the like even if the sensor element is scattered on the field. As a metal, copper, iron, aluminum, zinc, mercury, gold, silver, platinum, lithium, chromium, nickel, manganese, vanadium, rhodium, palladium, and the like are exemplified.

Similarly, the sensor element according to the embodiment preferably does not include an electronic component. While the electronic component is an essential configuration in the environment information collecting system in the related art, the sensor element according to the embodiment can realize its function without being provided with any electronic component. As the electronic component, a semiconductor device, a substrate, a printed substrate, an antenna, a battery, an electrical wire, a lead wire, and the like are exemplified.

The sensor element itself according to the embodiment preferably does not have a function of emitting an electromagnetic wave.

Although the size and the form of the sensor element according to the embodiment are not particularly limited, a sensor element in an example is in the form of a particle, and an average particle size is preferably 0.1 to 5 mm, is more preferably 0.3 to 3 mm, and is further preferably 1 to 2 mm. Here, the "particle size" refers to a diameter of a circle that circumscribes a projected image of the sensor element, and the aforementioned projected image is projected in a direction selected at random. The "average particle size" is acquired as an average numerical value of the aforementioned particle sizes of a group of sensor elements.

(Method for Manufacturing Sensor Element)

A method for manufacturing the sensor element is not particularly limited, and for example, the sensor element can be manufactured by molding the materials exemplified above. In a case in which the sensor element provided with the base materials exemplified above is manufactured, for example, a material of the base material and a solvent are first kneaded to obtain a raw material composition, the composition is molded by a known sheet molding method, and the thus obtained sheet is cut into a shape of the sensor element, thereby obtaining the sensor element. In a case in which the sensor element contains a pigment, the pigment may be added to the aforementioned raw material composition. As the sheet molding method, a melt extrusion molding method, a solution casting method, a calendering method, a co-extrusion method, a lamination method, and the like are exemplified.

(Packaged Body)

According to an embodiment of the invention, it is possible to provide a packaged body in which the sensor element is packaged by a packaging material. As the packaging material, a material that is ordinarily used as an agricultural material can be used, a packaging material for a fertilizer, soil, a soil conditioner, or the like can be used instead, for example, and a polyvinyl chloride sheet, a polyolefin sheet, and the like are exemplified. The number of the sensor elements included in one packaged body is not particularly limited, but may be equal to or greater than 1,000, may be 1,000 to 5,000,000,000,000, may be 10,000 to 1,000,000,000, or may be 100,000 to 10,000,000 per one packaged body on one example.

Including a large number of sensor elements in one packaged body makes it possible to acquire environment information using a large number of sensor elements at one time, and it is possible to collect the environment information with high resolution in a wide range, for example.

The packaged body according to the embodiment may include a description that the packaged body is used by being scattered in a target region where the aforementioned environment information is collected. That is, the packaged body according to the embodiment may include a description about a method of using the sensor elements. For the method of using the sensor elements, details in <Method of using sensor elements> described below can be referenced.

The description may be expressed on the surface of the packaged material, or the description may be expressed in the accompanying instructions, and the instructions and the sensor elements may be included in the packaged body together.

<Method of Using Sensor Elements>

According to an aspect of the invention, it is possible to provide a method of using sensor elements in which the aforementioned sensor elements are scattered in a target region where the aforementioned environment information is collected. For reception of electromagnetic waves obtained from the sensor elements and acquisition of environment information after the scattering, see the details in <Environment information collecting system>, <Aircraft>, and <Method for collecting environment information>.

Although the degree of the scattering of the sensor elements is not particularly limited, 1 to 100,000 of sensor elements may be scattered, 10 to 10,000 sensor elements may be scattered, or 100 to 5,000 sensor elements may be scattered per 1 $m^2$. By the degree of the scattering of the sensor elements per 1 $m^2$ falling within the aforementioned range, it is possible to collect the environment information with high resolution.

As a timing of the scattering of the sensor elements, for example, before seeding of agricultural crops raised in the target region, at the same time with the seeding, and a timing within one week after the seeding are exemplified, and it is preferable to scatter the sensor elements such that the sensor elements are located in the target region in a period from the seeding to the harvesting of the agricultural crops.

Although positions at which the sensor elements are scattered are preferably on the surface of a planting region in which the agricultural crops are raised, the sensor elements may be mixed into soil to such an extent that the electromagnetic waves from the sensor elements can be received. As the scattered positions relative to the agricultural crops, positions within 100 cm from main stems of the agricultural crops are preferable, positions within 10 cm are more preferable, and positions within 1 cm are further preferable.

(Aircraft)

Figure 6:
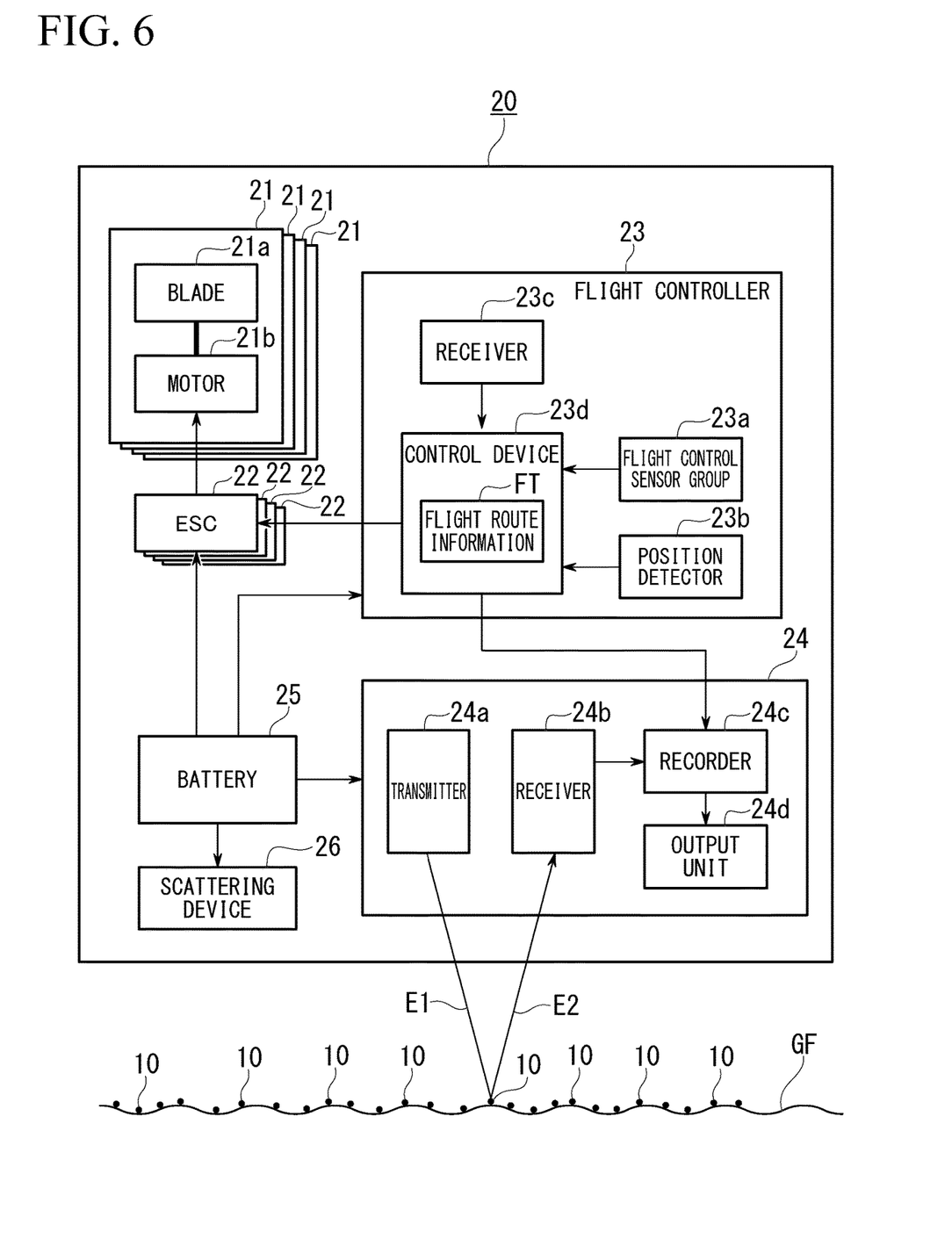
FIG. 6 is a block diagram illustrating main part configurations of a drone as an aircraft according to an embodiment of the invention.

FIG. 6 is a block diagram illustrating main part configurations of a drone as an aircraft according to an embodiment of the invention. As illustrated in FIG. 6, the drone 20 includes a plurality of rotors 21, a plurality of electric speed controllers (ESCs) 22, a flight controller 23, an environment information collecting device 24, a battery 25, and a scattering device 26. Note that the drone 20 exemplified in FIG. 6 includes four pairs of rotors 21 and ESCs 22.

Each rotor 21 includes a blade 21a and a motor 21b. The blade 21a is a so-called propeller and is for obtaining the buoyancy required for the drone 20 to fly. The blade 21a is coupled to a rotation shaft of the motor 21b, and rotation thereof is driven by the motor 21b. The blade 21a is formed using, for example, plastic, carbon, an ABS resin, or the like. Rotation of the motor 22b is driven by the ESC 22, and the motor 22 causes the blade 21a coupled to the rotation shaft to rotate. As the motor 22, a brushless motor, for example, can be used.

The plurality of ESCs 22 are provided to correspond to the plurality of rotors 21, respectively, and control rotation speeds of the motors 21b provided at the corresponding rotors 21 under control of the flight controller 23. Specifically, the ESCs 22 cause the motors 21b to rotate at speeds indicated by the flight controller FC. Note that in the drone 20 illustrated in FIG. 6, four ESCs 22 are provided to correspond to the four rotors 21, respectively, and are individually controlled by the flight controller 23.

The flight controller 23 includes a flight control sensor group 23a, a position detector 23b, a receiver 23c, and a control device 23d and performs flight control for the drone 20. The flight controller 23 can cause the drone 20 to autonomously fly (hereinafter, referred to as "auto-pilot") and can also cause the drone 20 to fly in accordance with a control signal transmitted from the outside (hereinafter, referred to as "manual manipulation"). Note that the flight controller 23 may be able to perform either the auto-pilot or the manual manipulation.

The flight control sensor group 23a is a sensor group required to perform flight control for the drone 20. The flight control sensor group 23a includes various sensors such as, for example, a three-axis acceleration sensor, a three-axis angular velocity sensor, an air pressure sensor (altitude sensor), and a geomagnetic sensor (azimuth sensor). The position detector 23b is provided with, for example, a positioning function such as a global positioning system (GPS) and detects position information of the drone 20 using the positioning function. Note that the method of detecting the position information of the drone 20 is not limited to the method using the positioning function of GPS and an arbitrary positioning method can be used.

The receiver 23c receives a control signal for controlling the flight of the drone 20 that is transmitted from the outside. For example, the receiver 23c receives a control signal that is transmitted as a wireless signal from a manipulation device (a device that is used to manually manipulate the drone 20), which is not illustrated in the drawing. Note that in a case in which the flight controller 23 can perform only auto-pilot, the receiver 23c is omitted.

The control device 23d acquires information indicating a flight state of the drone 20 from detection results of the flight control sensor group 23a and the position detector 23b and controls a posture when the drone 20 flies and a basic flight operation using the acquired information. The control device 23d can acquire, as the aforementioned information indicating the flight state, inclination and rotation of the body of the drone 20, a latitude and a longitude during flight, an altitude, an azimuth angle of the nose, position information of the drone 20 itself, and the like. The control device 23d causes the drone 20 to fly while individually controlling the ESCs 22, adjusting the rotation frequency of the rotors 21, and correcting disordered posture and position of the body, with reference to the aforementioned information indicating the flight state.

Also, the control device 23d can store flight route information FT required for auto-pilot. The flight route information FT is information including a flight route, a speed, an altitude, and the like. During the auto-pilot, the control device 23d adjusts the rotation frequency of the rotors 21 and causes the drone 20 to autonomously fly along the preset flight route, with reference to the aforementioned information indicating the flight state and the flight route information FT. On the other hand, during manual manipulation, the control device 23d adjusts the rotation frequency of the rotors 21 and causes the drone 20 to fly in accordance with an instruction from the outside, with reference to the aforementioned information indicating the flight state and the control signal received by the receiver 23c.

The environment information collecting device 24 includes the transmitter 24a, the receiver 24b, a recorder 24c, and an output unit 24d and collects environment information on the ground surface GF, for example. The transmitter 24a transmits the electromagnetic wave E1 with the specific wavelength to the ground surface GF as described above, and the receiver 24b receives the electromagnetic wave E2 obtained from the sensor elements 10 as described above (see FIG. 1). The recorder 24c includes a RAM (readable and writable memory) or the like and records a reception result of the receiver 24b. Here, the recorder 24c records the reception result of the receiver 24b along with the aforementioned information (for example, position information) indicating a flight state of the drone 20. In this manner, the reception result of the receiver 24b and the position information of the drone 20, for example, are recorded in the recorder 24c in an associated manner.

The output unit 24d outputs information recorded in the recorder 24c to the outside. For example, the output unit 24d may be configured to perform communication (wired communication or wireless communication) with an external device (for example, a personal computer, a smartphone, a tablet, or the like) and output information recorded in the recorder 24c to the outside, or may be configured to write various kinds of information in a detachable recording medium (for example, a non-volatile memory) and output information recorded in the recorder 24c to the outside.

The battery 25 supplies electric power required by the drone 20 to operate to each block of the drone 20. Specifically, the battery 25 supplies the electric power to the rotors 21 (motors 21b), the ESCs 22, the flight controller 23, the environment information collecting device 24, and the scattering device 26. The battery 25 may be, for example, a lithium ion battery or the like that can be attached to and detached from the body of the drone 20. Note that although one battery 25 is illustrated in FIG. 6, a battery for supplying electric power required by the drone 20 to fly and a battery for supplying electric power required for collecting environment information and causing the scattering device 26 to operate may be separately provided.

The scattering device 26 can accommodate the sensor elements 10 therein. The scattering device 26 scatters the sensor elements 10 accommodated therein. For example, the scattering device 26 scatters the sensor elements 10 in the target region TA or the like. Specifically, the scattering device 26 scatters the sensor elements 10 on the basis of a control signal (a control signal for providing an instruction for the scattering that is received by the receiver 23c) transmitted from the outside or a control signal for providing an instruction for the scattering that is output from the control device 23d. By including such a scattering device 26, for example, it is possible to recover the functions of the sensor element 10 lost through biodegradation by scattering the sensor elements 10 in the target region TA in a case in which the sensor elements 10 are biodegradable.

<Method for Collecting Environment Information>

Figure 7:
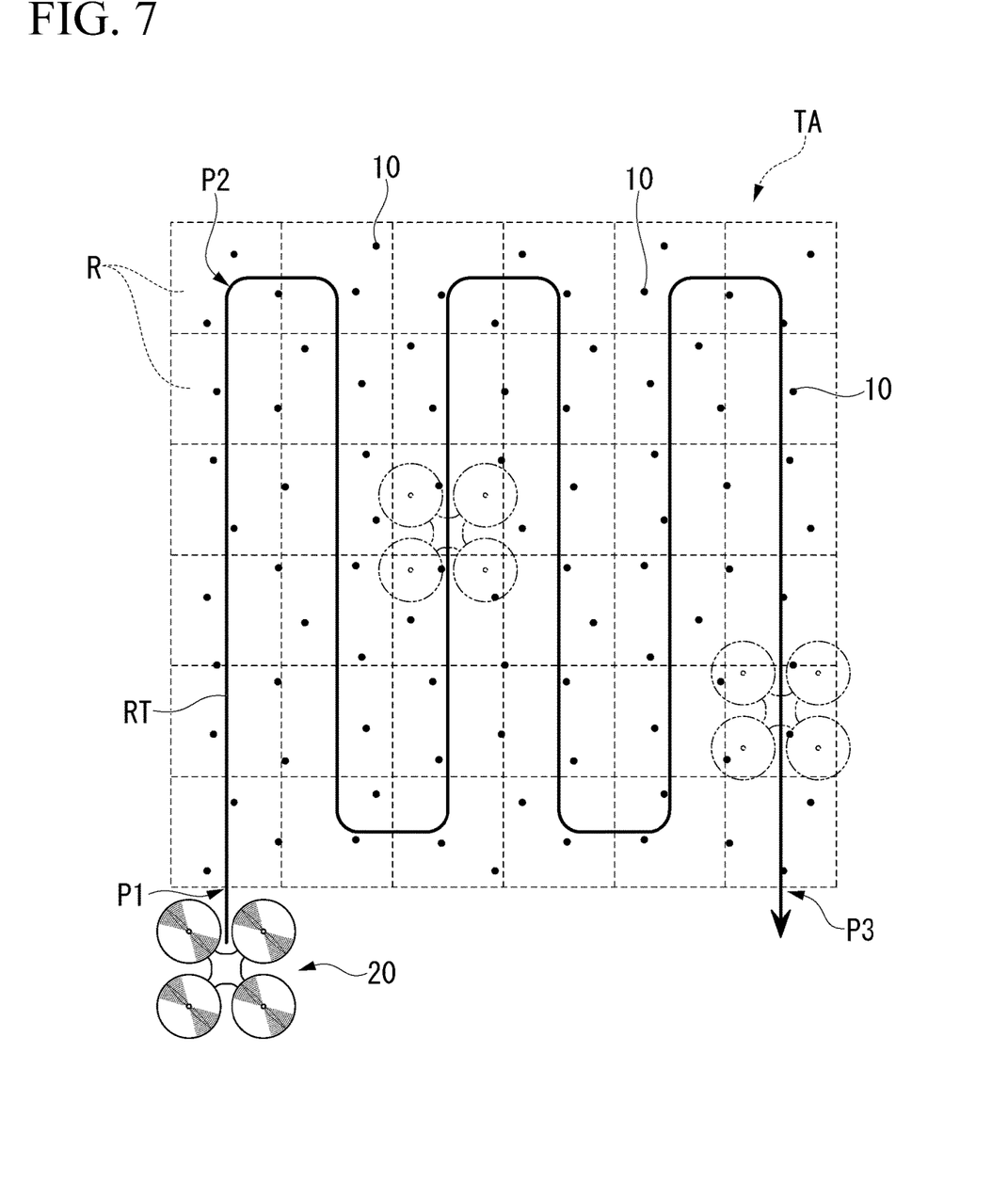
FIG. 7 is a plan view for explaining a method of collecting environment information using the environment information collecting system according to an embodiment of the invention.

FIG. 7 is a plan view for explaining a method for collecting environment information using the environment information collecting system according to an embodiment of the invention. Note that an example of a method for collecting environment information by causing the drone 20 to perform auto-pilot will be described here. The rectangular region illustrated in FIG. 7 represents the target region TA (a region set on the ground surface GF) in which environment information is collected using the drone 20. The sensor elements 10 are scattered in advance in the target region TA. Note that a reduced number of the sensor elements 10 are illustrated in FIG. 7 for convenience of illustration.

Also, the target region TA is sectioned into a plurality of grid-like subregions R as illustrated in FIG. 7. The subregions R represent units in which the environment information is collected. It is possible to improve resolution by setting the area of each subregion R to be small or to reduce the resolution by setting the area to be large. The size of each subregion R depends on properties of the receiver 24b provided in the environment information collecting device 24, a flight altitude of the drone 20, and the like. Here, the flight route RT of the drone 20 is set such that the drone 20 passes over all the subregions R in one stroke as illustrated in the drawing. Note that the altitude of the flight route RT of the drone 20 is assumed to be constant here for easy explanation.

Auto-pilot of the drone 20 is started by, for example, a user operating a manipulator provided in the drone 20, which is not illustrated, and providing an instruction for starting the auto-pilot. If the auto-pilot is started, the control device 23d provided in the flight controller 23 of the drone 20 acquires information indicating a flight state of the drone 20 from detection results of the flight control sensor group 23a and the position detector 23b and adjusts the rotation frequency of the rotors 21 with reference to the acquired information and the flight route information FT. In this manner, the drone 20 autonomously flies along the flight route RT illustrated in FIG. 7.

In parallel to the aforementioned operations, the transmitter 24a provided in the environment information collecting device 24 transmits the electromagnetic wave E1 with the specific wavelength to the target region TA, and the electromagnetic wave E2 obtained from the sensor elements 10 is received by the receiver 24b. The reception result of the receiver 24b is recorded along with the information (for example, position information) indicating the flight state of the drone 20 that is acquired by the control device 23d. In this manner, the reception result of the electromagnetic wave E2 obtained from the sensor elements 10 when the drone 20 autonomously flies along the flight route RT is recorded in the recorder 24c along with the position information and the like.

Figure 8:
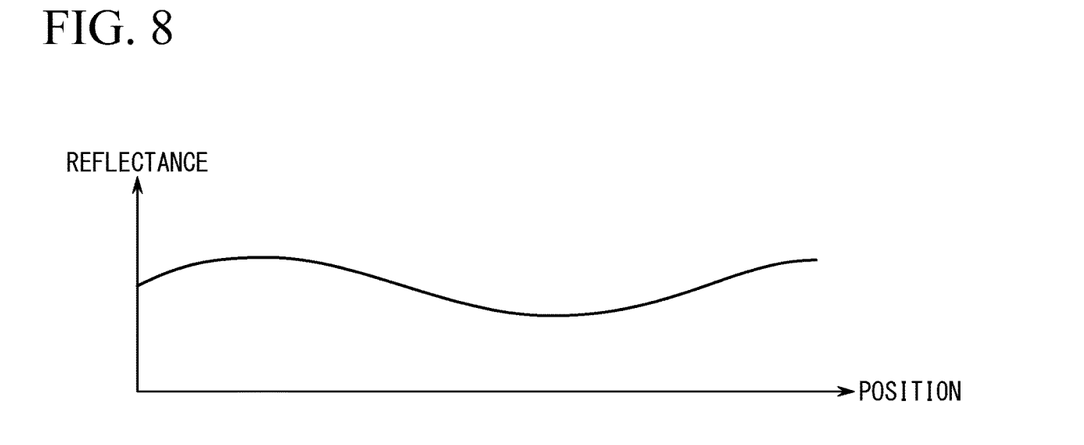
FIG. 8 is a diagram illustrating an example of environment information collected according to an embodiment of the invention.

FIG. 8 is a diagram illustrating an example of environment information collected according to an embodiment of the invention. Note that the environment information illustrated in FIG. 8 is obtained, for example, when the drone 20 flies along the flight route RT from the position P1 to the position P2 in FIG. 7 in a case where the sensor elements 10 in which the reflection properties and transmission properties with respect to the electromagnetic wave E1 change in accordance with an ambient temperature are scattered in the target region TA. Here, since the sensor elements 10 scattered in the target region T1 have reflection properties and the transmission properties with respect to the electromagnetic wave E1 that change in accordance with the ambient temperature, it is possible to obtain the ambient temperatures of the sensor elements 10 as long as it is possible to obtain the reflectance of the electromagnetic wave E1 (a ratio between reception results of the electromagnetic wave E1 and the electromagnetic wave E2). That is, collecting the reflectance of the electromagnetic wave E1 is synonymous with collecting the ambient temperatures of the sensor elements 10.

The drone 20 flies along the flight route RT from the position P1 to the position P3 in FIG. 7, thereby obtaining reflectance over the entire length of the flight route RT (the reflectance along the flight route RT). As illustrated in FIG. 7, since the flight route RT is set so as to pass above all subregions R in one stroke, it is possible to obtain the reflectance (temperature) in all subregions R. In this manner, it is possible to obtain a temperature distribution (temperature distribution in a plane) within the target region TA set on the ground surface GF.

Note that the reflectance in the subregions R may be obtained by performing a predetermined arithmetic operation (for example, an averaging operation) on reflectance obtained during passing above each subregion R among reflectance successively obtained along the flight route RT, for example. Alternatively, the reflectance in the subregion R may be obtained by acquiring reflectance once above each subregion R (discretely acquiring reflectance) instead of successively obtaining the reflectance along the flight route RT.

As described above, although collecting the reflectance of the electromagnetic wave E1 is synonymous with collecting ambient temperatures of the sensor elements 10, a process of obtaining the ambient temperatures of the sensor elements 10 from the reflectance of the electromagnetic wave E1 may be performed inside the drone 20 or may be performed outside the drone 20. In a case in which the process is performed inside the drone 20, for example, it is only necessary to provide an arithmetic operator for converting a reception result of the receiver 24b (indicating the reflectance of the electromagnetic wave E1) into temperatures in the environment information collecting device 24. In this case, the temperatures obtained by the arithmetic operator are recorded in the recorder 24c along with position information and the like. In a case in which the process is performed outside the drone 20, the information recorded in the recorder 24c is output to an external device (for example, a personal computer) from the output unit 24d, and the temperatures are obtained by the external device.

As described above, according to the embodiment, the drone 20 (the transmitter 24a of the environment information collecting device 24) transmits the electromagnetic wave E1 with a specific wavelength to the target region TA in which the sensor elements 10 are scattered on the ground GF, and the drone 20 (the receiver 24b of the environment information collecting device 24) receives the electromagnetic wave E2 obtained from the sensor elements 10, thereby collecting environment information (for example, water content, a temperature, pH, the amount of sunshine, and the like) on the ground surface GF. Therefore, it is possible to obtain the environment information on the surface of the earth or a surface layer of the earth in a short period of time in an easy manner without any need of great effort as in the related art.

Although the environment information collecting system and the aircraft according to the embodiment of the invention have been described above, the invention is not limited to the aforementioned embodiment, and modifications can be freely made within the scope of the invention. For example, although the drone 20 as an unmanned aircraft has been exemplified as the aircraft in the aforementioned embodiment, the aircraft is not limited to the unmanned aircraft and may be a manned aircraft. Note that the unmanned aircraft may be an arbitrary device that can be caused to fly through remote control or an autopilot among an airplane, a rotary wing aircraft, a glider, an airship, or another machine with a structure on which no man can ride.

Also, the example in which the sensor elements 10 are scattered on the ground surface GF to collect environment information on the ground surface GF has been described in the aforementioned embodiment. However, the sensor elements 10 may be scattered in a surface of a sea, a surface of a lake, a surface of a river, or the like to collect environment information on the surface of the sea, the surface of the lake, the surface of the river, or the like. Also, the sensor elements 10 may be scattered in the ground, in water, in a sea, or the like to collect environment information in the ground, in the water, in the sea, or the like as long as it is possible to transmit and receive the electromagnetic waves E1 and E2. That is, the environment information collecting system according to the invention can collect environment information on the surface of the earth or a surface layer of the earth.

Also, the example in which the drone 20 includes the transmitter 24a that transmits the electromagnetic wave E1 with a specific wavelength has been described in the aforementioned embodiment. However, in a case in which the electromagnetic wave E1 with the specific wavelength is obtained from solar light, it is possible to omit the transmitter 24a. Also, in a case in which the sensor elements 10 are elements in which light emitting properties change in accordance with an ambient environment, the electromagnetic wave E2 received by the receiver 24b is self-light emission emitted from the sensor elements 10, and it is thus possible to omit the transmitter 24a for transmitting the electromagnetic wave E1 with the specific wavelength. Note that in a case in which it is not necessary to scatter the sensor elements 10, it is also possible to omit the scattering device 26.

Also, the sensor elements that are scattered by being mixed into a fertilizer or a pesticide have been exemplified and described as the sensor elements 10 used in the field of agriculture in the aforementioned embodiment. However, sensor elements that are caused to contain fertilizer components or the like therein, for example, can also be used as the sensor elements 10 used in the field of agriculture. In a case in which such sensor elements 10 are scattered on farmland, the fertilizer components contained therein are released to the outside and penetrate into the soil of the farmland, but the sensor elements 10 from which the fertilizer components have been released do not lose functions as sensor elements.

[Supplementary Note]

In order to solve the aforementioned problems, a sensor element according to an aspect of the invention and a packaged body according to an aspect of the invention described in (1) to (20) below are provided.

(1) A sensor element that is used to collect environment information on a surface of the earth or a surface layer of the earth by being scattered in a target region where the environment information is collected, wherein at least one of reflection properties, transmission properties, absorption properties, or luminescence properties with respective to an electromagnetic wave with a specific wavelength, or light emitting properties changes in accordance with an environment.

(2) The sensor element according to (1) described above, wherein the environment information is at least one of water content, temperature, or pH.

(3) The sensor element according to (2) described above, wherein the environment information is pH, and
wherein the sensor element includes a substance in which at least one of the reflection properties, the transmission properties, the absorption properties, or the luminescence properties with respect to the electromagnetic wave with the specific wavelength, or the light emitting properties changes in accordance with a change in pH.

(4) The sensor element according to (3) described above, wherein the substance is litmus, bromothymol blue, bromophenol blue, bromocresol purple, phenol red, phenolphthalein, methyl orange, methyl red, methyl yellow, methyl violet, thymol blue, or thymol phthalein.

(5) The sensor element according to (2) described above, wherein the environment information is at least one of water content or temperature, and wherein a shape of the sensor element changes in accordance with a change in at least one of the water content or the temperature.

(6) The sensor element according to claim (5) described above, wherein the environment information is the temperature, wherein the sensor element includes a first base material and a second base material, and wherein a coefficient of thermal expansion of the first base material depending on the temperature differs from a coefficient of thermal expansion of the second base material depending on the temperature.

(7) The sensor element according to (6) described above, wherein the coefficient of thermal expansion of the first base material depending on the temperature is less than 10, and wherein the coefficient of thermal expansion of the second base material depending on the temperature is equal to or greater than 10.

(8) The sensor element according to (7) described above, wherein the first base material is polystyrene, an AS resin, polycarbonate, polymethyl methacrylate, a phenol resin, or an epoxy resin, and wherein the second base material is polyethylene, polyvinylidene chloride, polyvinylidene fluoride, polyethylene terephthalate, or cellulose acetate.

(9) The sensor element according to (5) described above, wherein the environment information is the water content, wherein the sensor element includes a third base material and a fourth base material, and wherein a rate of change in volume depending on water retention of the third base material differs from a rate of change in volume depending on water retention of the fourth base material.

(10) The sensor element according to (9) described above, wherein the rate of change in volume depending on the water retention of the fourth base material is greater than the rate of change in volume depending on the water retention of the third base material.

(11) The sensor element according to (10) described above, wherein the third base material is a cellulose film, and wherein the fourth base material is a pectin film.

(12) The sensor element according to (1) to (11) described above, further including a fluorescent pigment.

(13) The sensor element according to (12) described above, wherein the fluorescent pigment is acridine orange, auramine O, calcofluor white, ethidium bromide, fluorescein isothiocyanate, Hoechst 33258, or Rhodamine B.

(14) The sensor element according to (1) to (12) described above, wherein the sensor element is made of a biodegradable material.

(15) The sensor element according to (14) described above, wherein the biodegradable material is polylactic acid, polycaprolactone, polyhydroxyalkanoate, a polyhydroxy butyric acid, a polyglycolic acid, polyvinyl alcohol, casein, starch, esterified starch, cellulose, pectin, agar, or gelatin.

(16) The sensor element according to (1) to (15) described above, wherein the sensor element does not substantially include any metal.

(17) The sensor element according to (1) to (16) described above, wherein the sensor element does not include any electronic component.

(18) The sensor element according to (1) to (17) described above, wherein an average particle size of the sensor element is 0.1 to 5 mm.

(19) A packaged body, wherein the sensor element according to (1) to (18) is packaged with a packaging material.

(20) The packaged body according to (19) described above, further includes a description that the sensor element is used by being scattered in the target region in which the environment information is collected.

[Supplementary Note]

The sensor element according to an aspect of the invention and the packaged body according to an aspect of the invention described in (1) to (13) above relate to an environment information collecting system and an aircraft described in [1] to [11] below.

[1] An environment information collecting system that collects environment information on the surface of the earth or a surface layer of the earth, the system including: sensor elements, which are scattered in a target region in which the environment information is collected, in which at least one of reflection properties, transmission properties, absorption properties, or luminescence properties with respect to an electromagnetic wave with a specific wavelength, or light emitting properties changes in accordance with an environment; and an aircraft that receives the electromagnetic waves obtained from the sensor element and collects the environment information in the target region.

[2] The environment information collecting system according to [1] described above, in which the aircraft includes a receiver that receives the electromagnetic waves obtained from the sensor element and a recorder that records a result of reception of the receiver.

[3] The environment information collecting system according to [1] or [2] described above, wherein the aircraft includes a transmitter that transmits the electromagnetic wave with the specific wavelength to the target region.

[4] The environment information collecting system according to any one of [1] to [3] described above, in which the electromagnetic wave with the specific wavelength is a millimeter wave, a terahertz wave, an infrared ray, a visible ray, an ultraviolet ray, or an X-ray.

[5] The environment information collecting system according to any one of [1] to [4] described above, wherein the electromagnetic wave obtained from the sensor element is an electromagnetic wave with a wavelength that is different from the specific wavelength of the electromagnetic wave.

[6] The environment information collecting system according to any one of [1] to [5] described above, in which the aircraft includes a plurality of rotary wings, and a flight controller that controls the rotary wings in accordance with flight route information indicating a preset flight route and causes the aircraft to autonomously fly along the flight route.

[7] The environment information collecting system according to any one of [1] to [6] described above, in which the aircraft includes a scattering device that scatters the sensor element in the target region.

[8] The environment information collecting system according to any one of [1] to [7] described above, in which the sensor element includes a fertilizer component.

[9] An aircraft that collects environment information on the surface of the earth or a surface layer of the earth, the aircraft includes: a receiver that receives electromagnetic waves obtained from sensor elements, which are scattered in a target region in which the environment information is collected, in which at least one of reflection properties, transmission properties, absorption properties, or luminescence properties with respect to an electromagnetic wave with a specific wavelength, or light emitting properties changes in accordance with an environment, and a recorder that records a result of reception of the receiver.

[10] The aircraft according to [9] described above, further including: a transmitter that transmits the electromagnetic wave with the specific wavelength to the target region.

[11] The aircraft according to [9] or [10] described above, further including: a scattering device that scatters the sensor elements in the target region.

According to the invention, there is an advantage that it is possible to obtain environment information on the surface of the earth or a surface layer of the earth in a short period of time in an easy manner without any need of great effort.

As used herein, the following directional terms "front, back, above, downward, right, left, vertical, horizontal, below, transverse, row and column" as well as any other similar directional terms refer to those instructions of a device equipped with the present invention. Accordingly, these terms, as utilized to describe the present invention should be interpreted relative to a device equipped with the present invention.

The term "configured" is used to describe a component, unit or part of a device includes hardware and/or software that is constructed and/or programmed to carry out the desired function.

Moreover, terms that are expressed as "means-plus function" in the claims should include any structure that can be utilized to carry out the function of that part of the present invention.

The term "unit" is used to describe a component, unit or part of a hardware and/or software that is constructed and/or programmed to carry out the desired function. Typical examples of the hardware may include, but are not limited to, a device and a circuit.

While preferred embodiments of the present invention have been described and illustrated above, it should be understood that these are examples of the present invention and are not to be considered as limiting. Additions, omissions, substitutions, and other modifications can be made without departing from the scope of the present invention. Accordingly, the present invention is not to be considered as being limited by the foregoing description, and is only limited by the scope of the claims.

What is claimed is:
1. A sensor element comprising:
first and second portions respectively comprising first and second base materials made of a biodegradable material; and
a fertilizer contained in the first and second base materials,
wherein at least one of reflection properties, transmission properties, absorption properties, or luminescence properties of the sensor element with respect to an electromagnetic wave with a specific wavelength, or light emitting properties of the sensor element changes in accordance with an environment of the first and second base materials, wherein the first base material and the second base material are arranged in layers, wherein a shape of the first and second base materials changes in accordance with a change in water content in the first and second base materials, and wherein a rate of change in volume depending on water retention of the second base material is greater than a rate of change in volume depending on water retention of the first base material.

2. The sensor element according to claim 1, wherein the sensor element includes a substance in which at least one of the reflection properties, the transmission properties, the absorption properties, or the luminescence properties of the sensor element with respect to the electromagnetic wave with the specific wavelength, or the light emitting properties of the sensor element changes in accordance with a change in pH.

3. The sensor element according to claim 2, wherein the substance is litmus, bromothymol blue, bromophenol blue, bromocresol purple, phenol red, phenolphthalein, methyl orange, methyl red, methyl yellow, methyl violet, thymol blue, or thymol phthalein.

4. The sensor element according to claim 1, wherein a coefficient of thermal expansion of the first base material depending on temperature differs from a coefficient of thermal expansion of the second base material depending on the temperature.

5. The sensor element according to claim 4, wherein the coefficient of thermal expansion of the first base material depending on the temperature is less than 10, and wherein the coefficient of thermal expansion of the second base material depending on the temperature is equal to or greater than 10.

6. The sensor element according to claim 5, wherein the first base material is polystyrene, an AS resin, polycarbonate, polymethyl methacrylate, a phenol resin, or an epoxy resin, and wherein the second base material is polyethylene, polyvinylidene chloride, polyvinylidene fluoride, polyethylene terephthalate, or cellulose acetate.

7. The sensor element according to claim 1, wherein the first base material is a cellulose film, and wherein the second base material is a pectin film.

8. The sensor element according to claim 1, further including a fluorescent pigment.

9. The sensor element according to claim 8, wherein the fluorescent pigment is acridine orange, auramine O, calcofluor white, ethidium bromide, fluorescein isothiocyanate, Hoechst 33258, or Rhodamine B.

10. The sensor element according to claim 1, wherein the biodegradable material is polylactic acid, polycaprolactone, polyhydroxyalkanoate, a polyhydroxy butyric acid, a polyglycolic acid, polyvinyl alcohol, casein, starch, esterified starch, cellulose, pectin, agar, or gelatin.

11. The sensor element according to claim 1, wherein an average particle size of the sensor element is 0.1 to 5 mm.

12. A sensor element comprising first and second portions respectively comprising first and second base materials made of a biodegradable material; and a fertilizer contained in the first and second base materials, wherein at least one of reflection properties, transmission properties, absorption properties, or luminescence properties of the sensor element with respect to an electromagnetic wave with a specific wavelength, or light emitting properties of the sensor element changes in accordance with an environment of the first and second base materials, wherein the first base material and the second base material are arranged in layers, wherein a shape of the first and second base materials changes in accordance with a change in water content in the first and second base materials, wherein a rate of change in volume depending on water retention of the first base material differs from a rate of change in volume depending on water retention of the second base material, and wherein the sensor element does not substantially include any metal.

13. A sensor element comprising first and second portions respectively comprising first and second base materials made of a biodegradable material; and a fertilizer contained in the first and second base materials, wherein at least one of reflection properties, transmission properties, absorption properties, or luminescence properties of the sensor element with respect to an electromagnetic wave with a specific wavelength, or light emitting properties of the sensor element changes in accordance with an environment of the first and second base materials, wherein the first base material and the second base material are arranged in layers, wherein a shape of the first and second base materials changes in accordance with a change in water content in the first and second base materials, wherein a rate of change in volume depending on water retention of the first base material differs from a rate of change in volume depending on water retention of the second base material, and wherein the sensor element does not comprise any electronic component.

* * * * *